（12） United States Patent
Watanabe et al.

(10) Patent No.: US 9,931,051 B2
(45) Date of Patent: Apr. 3, 2018

(54) MAGNETIC RESONANCE IMAGING APPARATUS AND MEDICAL IMAGE DIAGNOSIS APPARATUS

(71) Applicant: TOSHIBA MEDICAL SYSTEMS CORPORATION, Otawara-shi (JP)

(72) Inventors: Kota Watanabe, Otawara (JP); Hiromitsu Takamori, Otawara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 882 days.

(21) Appl. No.: 14/291,232

(22) Filed: May 30, 2014

(65) Prior Publication Data

US 2014/0266204 A1     Sep. 18, 2014

Related U.S. Application Data

(63) Continuation of application No. PCT/JP2013/050567, filed on Jan. 15, 2013.

(51) Int. Cl.
*A61B 5/055* (2006.01)
*A61B 6/04* (2006.01)
(Continued)

(52) U.S. Cl.
CPC ......... *A61B 5/0555* (2013.01); *A61B 5/0035* (2013.01); *A61B 5/055* (2013.01);
(Continued)

(58) Field of Classification Search
CPC ........... A61B 5/055; A61B 6/04; A61B 6/032; A61B 6/035; A61B 6/037; A61B 6/4417;
(Continued)

(56) References Cited

U.S. PATENT DOCUMENTS 7,702,375 B2   4/2010   Böninger et al.
7,852,080 B2   12/2010  Takamori et al.
(Continued)

FOREIGN PATENT DOCUMENTS

CN   1550207 A    12/2004
CN   101185572 A   5/2008
(Continued)

OTHER PUBLICATIONS

Office Action dated Oct. 12. 2015 in CN 201380000183.0.
(Continued)

*Primary Examiner* — Gregory H Curran
(74) *Attorney, Agent, or Firm* — Nixon & Vanderhye P.C.

(57) ABSTRACT

A magnetic resonance imaging apparatus according to the present embodiments comprises a gantry device, a front light source and an exterior casing of the gantry device. The gantry device has a bore serving as a space where a magnetic resonance image is captured, with the gantry device being configured to acquire, when a subject placed on a couchtop has been moved into the bore by a couch device configured to move the couchtop, a magnetic resonance signal from the subject. The front light source is provided in surroundings of a front opening, with the front opening being an opening of the bore positioned at front of the couch device. The exterior casing of the gantry device, with a portion of the exterior casing being illuminated by light emitted from the front light source, is made of a transparent or translucent material.

18 Claims, 10 Drawing Sheets

(51) Int. Cl.
*A61B 5/00* (2006.01)
*A61B 6/03* (2006.01)
*A61B 6/00* (2006.01)

(52) U.S. Cl.
CPC ................ *A61B 6/04* (2013.01); *A61B 6/032* (2013.01); *A61B 6/035* (2013.01); *A61B 6/037* (2013.01); *A61B 6/4417* (2013.01); *A61B 6/4435* (2013.01)

(58) Field of Classification Search
CPC .... A61B 6/4435; A61B 5/0555; A61B 5/0035
See application file for complete search history.

(56) References Cited

U.S. PATENT DOCUMENTS

2005/0004444 A1* 1/2005 Boninger ............. A61B 5/0555
600/407

2008/0204017 A1 8/2008 Takamori et al.

FOREIGN PATENT DOCUMENTS

| | | |
|---|---|---|
| JP | 8-84726 | 4/1996 |
| JP | 2544637 | 5/1997 |
| JP | 2004-89621 | 3/2004 |
| JP | 2008-149118 | 7/2008 |
| JP | 2011-024803 | 2/2011 |

OTHER PUBLICATIONS

Office Action dated Nov. 26, 2014 in CN 201380000183.0.
International Search Report for PCT/JP2013/050567, dated Feb. 12, 2013.
Written Opinion of the ISA for PCT/JP2013/050567, dated Feb. 12, 2013.

* cited by examiner

FIG.3
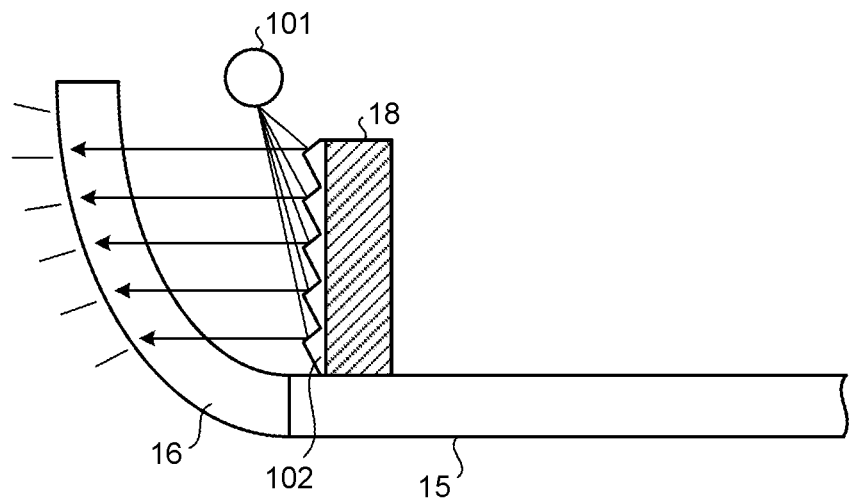
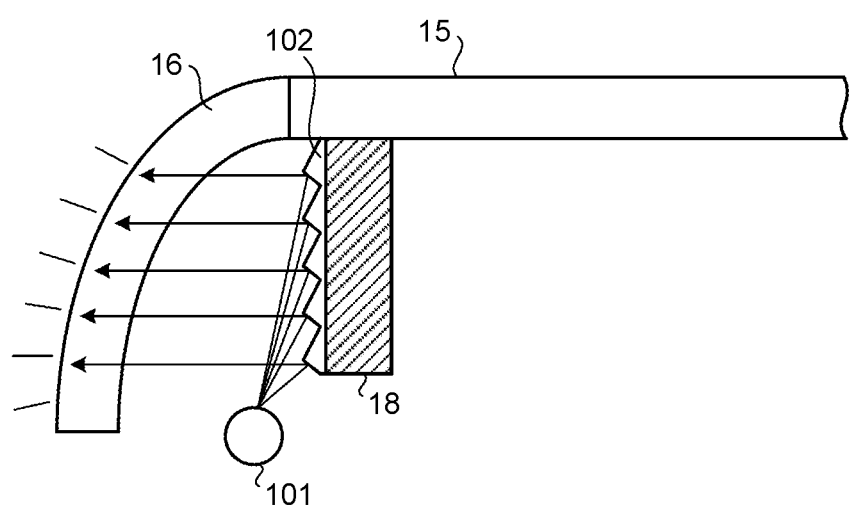

FIG.5
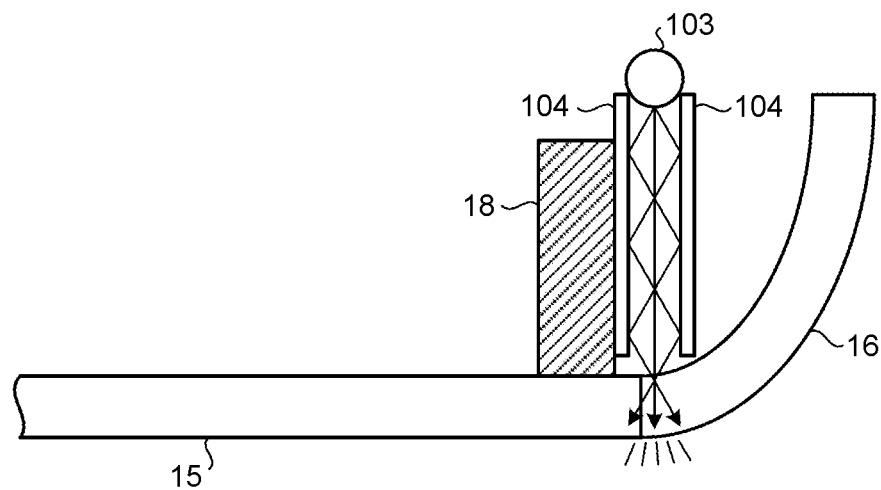
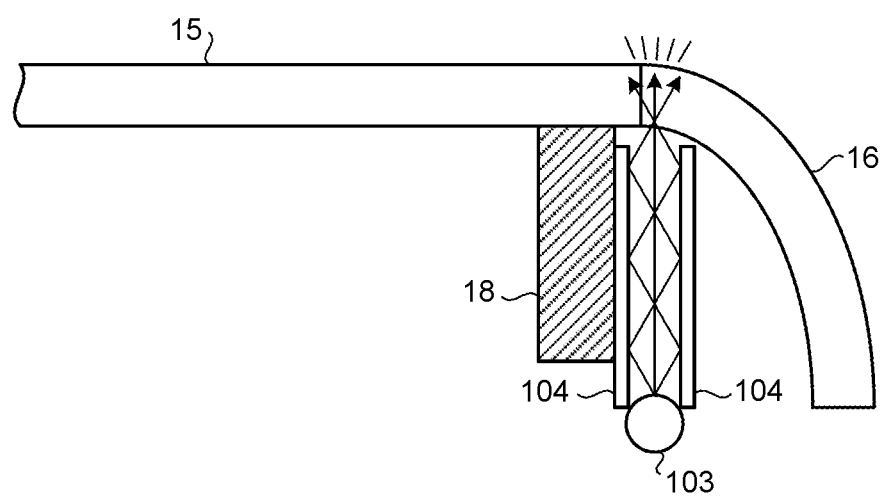

ADJUST TRANSMITTANCE USING DENSITY OF DOTS

| 101 | 105 | 106 | 103 |
|-----|-----|-----|-----|
| OFF | ON(M) | ON(M) | OFF |

MAGNETIC RESONANCE IMAGING APPARATUS AND MEDICAL IMAGE DIAGNOSIS APPARATUS

CROSS-REFERENCE TO RELATED APPLICATIONS

This application is a continuation of PCT international application Ser. No. PCT/JP2013/050567 filed on Jan. 15, 2013 which designates the United States, incorporated herein by reference, and which claims the benefit of priority from Japanese Patent Application No. 2012-005501, filed on Jan. 13, 2012, the entire contents of which are incorporated herein by reference.

FIELD

Embodiments described herein relate generally to a magnetic resonance imaging apparatus and a medical image diagnosis apparatus.

BACKGROUND

During a Magnetic Resonance Imaging (MRI) image-capturing process using an MRI apparatus, a subject is moved into a bore of a gantry device, while being placed on a couchtop. The gantry device generates a high-frequency magnetic field and a gradient magnetic field on the basis of a pulse sequence corresponding to an image-capturing condition and acquires magnetic resonance signals thereby emitted from the subject.

The gantry device includes, for example, a magnetostatic field magnet that generates a uniform magnetostatic field in the bore and a gradient coil that is provided on the inside of the magnetostatic field magnet and generates a gradient magnetic field in the bore. The magnetostatic field magnet, the gradient coil, and so forth are provided on the outside of a bore tube securing a bore space. Furthermore, a rail etc. on which the couchtop is moved is provided in the bore of the gantry device.

In the gantry device, noise is generated mainly from the gradient coil because of mechanical operations or electromagnetic forces during data acquiring processes. To improve comfortability of subjects during image-capturing processes, such MRI apparatuses that are able to inhibit the noise generated by the gantry device are being developed. Examples of such MRI apparatuses include an apparatus in which the sound released from end faces of an Actively Shielded Gradient Coil (ASGC) is blocked by covering the end faces of the ASGC with lids (sound-blocking lids) that are configured by using a sound-blocking material or a sound-absorbing material. Examples of such MRI apparatuses also include an apparatus in which the gradient coil is stored in a vacuum container.

Furthermore, in recent years, to improve comfortability of subjects during image-capturing processes, such an MRI apparatus that has a large aperture so as to physically make the space inside the bore as large as possible has been developed. However, in view of performance of RF coils and image quality of MRI images, there is a limit to designing apertures of bores to be large.

Because there is a limit to securing physical spaces of bores, attempts have been made by arranging the wall of a bore to be in a bright color such as white and by brightening the wall of a bore with illumination, in order to improve comfortability. However, even with those methods, it is not necessarily possible to prevent subjects from feeling insecure when the subjects are inserted into a bore, and the degree of comfortability which subjects experience when having been moved into a bore was not necessarily sufficient.

BRIEF DESCRIPTION OF THE DRAWINGS

FIG. 3 is a first drawing for explaining front light sources and front reflecting units according to the embodiment;

FIG. 5 is a first drawing for explaining rear light sources and rear reflecting units according to the embodiment;

DETAILED DESCRIPTION

A magnetic resonance imaging apparatus according to the present embodiments comprises a gantry device, a front light source and an exterior casing of the gantry device.

The gantry device has a bore serving as a space where a magnetic resonance image is captured, with the gantry device being configured to acquire, when a subject placed on a couchtop has been moved into the bore by a couch device configured to move the couchtop, a magnetic resonance signal from the subject.

The front light source is provided in surroundings of a front opening, with the front opening being an opening of the bore and with the front opening being an opening of the bore positioned at front of the couch device.

A portion of the exterior casing is illuminated by light emitted from the front light source. The portion of the exterior casing is made of a transparent or translucent material.

Exemplary embodiments of a magnetic resonance imaging apparatus will be explained in detail below, with reference to the accompanying drawings. In the following sections, the magnetic resonance imaging apparatus will be referred to as the "MRI apparatus".

Figure 1:
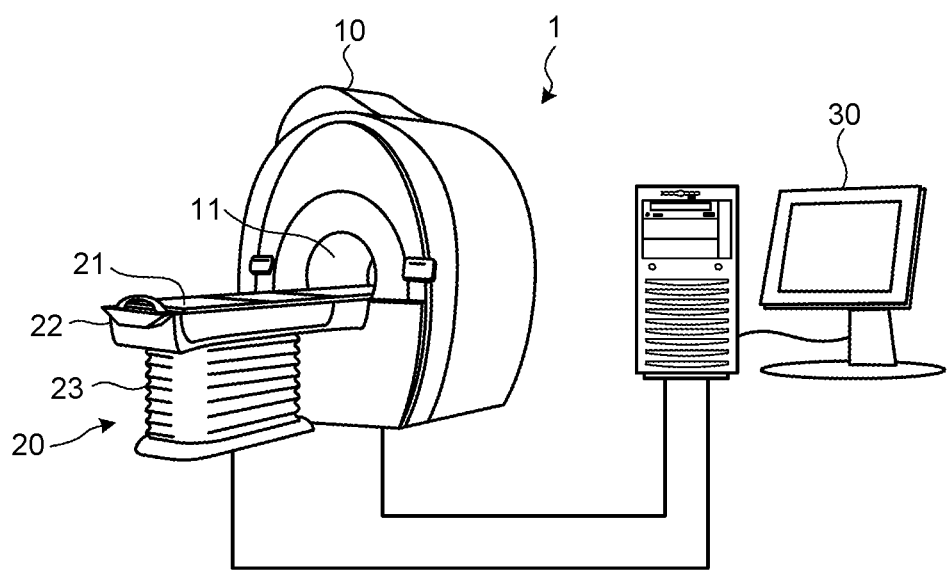
FIG. 1 is a drawing for explaining an exemplary overall configuration of an MRI apparatus according to an embodiment.

First, an exemplary overall configuration of an MRI apparatus according to an embodiment will be explained. FIG. 1 is a drawing for explaining the exemplary overall configuration of the MRI apparatus according to the present embodiment. As shown in FIG. 1, an MRI apparatus 1 according to the present embodiment includes a gantry device 10, a couch device 20, and a controlling device 30.

The gantry device 10 has a bore 11 serving as a space where a magnetic resonance image (an MRI image) is captured. Furthermore, although not shown in FIG. 1, the gantry device 10 includes: a magnetostatic field magnet that generates a magnetostatic field on the inside of the bore 11; a gradient coil that generates a gradient magnetic field; and a transmission Radio Frequency (RF) coil that emits an RF pulse onto a subject placed in the magnetic field generated by the magnetostatic field magnet etc. The gantry device 10 may include a reception RF coil that receives a magnetic resonance signal emitted from the subject due to the RF pulse emitted. Alternatively, an RF coil that serves as both a transmission RF coil and a reception RF coil may be provided in the gantry device 10.

The couch device 20 is a device that has a couchtop 21 to be inserted into the bore 11, together with the subject. The couch device 20 includes a couchtop supporting unit 22 that supports the couchtop 21, with the couchtop supporting unit 22 being movable into the bore 11 and a raising/lowering mechanism 23 that supports the couchtop supporting unit 22 so as to be movable in up and down directions.

The controlling device 30 is a device that exercises overall control of the MRI apparatus 1. On the basis of an image-capturing condition specified by an operator, the controlling device 30 drives the gradient coil, the transmission RF coil etc. that are included in the gantry device 10. Also, on the basis of an instruction from the operator, the controlling device 30 controls operations of the couchtop supporting unit 22, the raising/lowering mechanism 23, the couchtop 21 etc. that are included in the couch device 20.

Next, operations of the MRI apparatus 1 during an MRI image-capturing process will be explained briefly. First, before an image-capturing process, the couchtop supporting unit 22 of the couch device 20 is stopped at an initial position that is on the outside of the gantry device 10 and is lower than the bore 11. To start an image-capturing process, the subject is first placed on the couchtop 21. Next, on the basis of an instruction from the operator, the couchtop supporting unit 22 is moved upward to a height equal to substantially the center of the bore 11 of the gantry device 10. Subsequently, the couchtop 21 is moved into the bore 11, together with the subject.

When the couchtop 21 has been moved into the bore 11, the image-capturing process is started. More specifically, first, in the bore 11 of the gantry device 10, the transmission RF coil emits an RF pulse toward the subject. Due to the RF pulse, nuclear magnetic resonance signals are emitted from the subject. The nuclear magnetic resonance signals are acquired by a reception RF coil attached to the subject etc. and are transmitted to an image processing apparatus (now shown). Next, the image processing apparatus performs a predetermined calculation process on the basis of the transmitted signals so as to reconstruct an MRI image of the subject.

When the image-capturing process is finished, the couchtop 21 is moved to the outside of the bore 11, together with the subject. Subsequently, the couchtop supporting unit 22 is moved downward to the initial position. As described above, the gantry device 10 is configured to acquire the magnetic resonance signals from the subject P, when the subject placed on the couchtop 21 has been moved into the bore 11 by the couch device 20 configured to move the couchtop 21.

The overall configuration and the operations during the image-capturing process of the MRI apparatus 1 have thus been explained. During an image-capturing process, the gantry device 10 has noise that is mainly generated from the gradient coil. To cope with this problem, for example, end faces of an Actively Shielded Gradient Coil (ASGC) have conventionally been covered by lids (sound-blocking lids) configured by using a sound-blocking material or a sound-absorbing material, so as to block the sound released from the end faces of the ASGC. Furthermore, to improve comfortability of subjects during image-capturing processes, the bore 11 has conventionally been designed so as to physically make the space inside the bore 11 as large as possible. However, in view of performance of RF coils and image quality of MRI images, there is a limit to designing the aperture of the bore 11 to be large.

Figure 2:
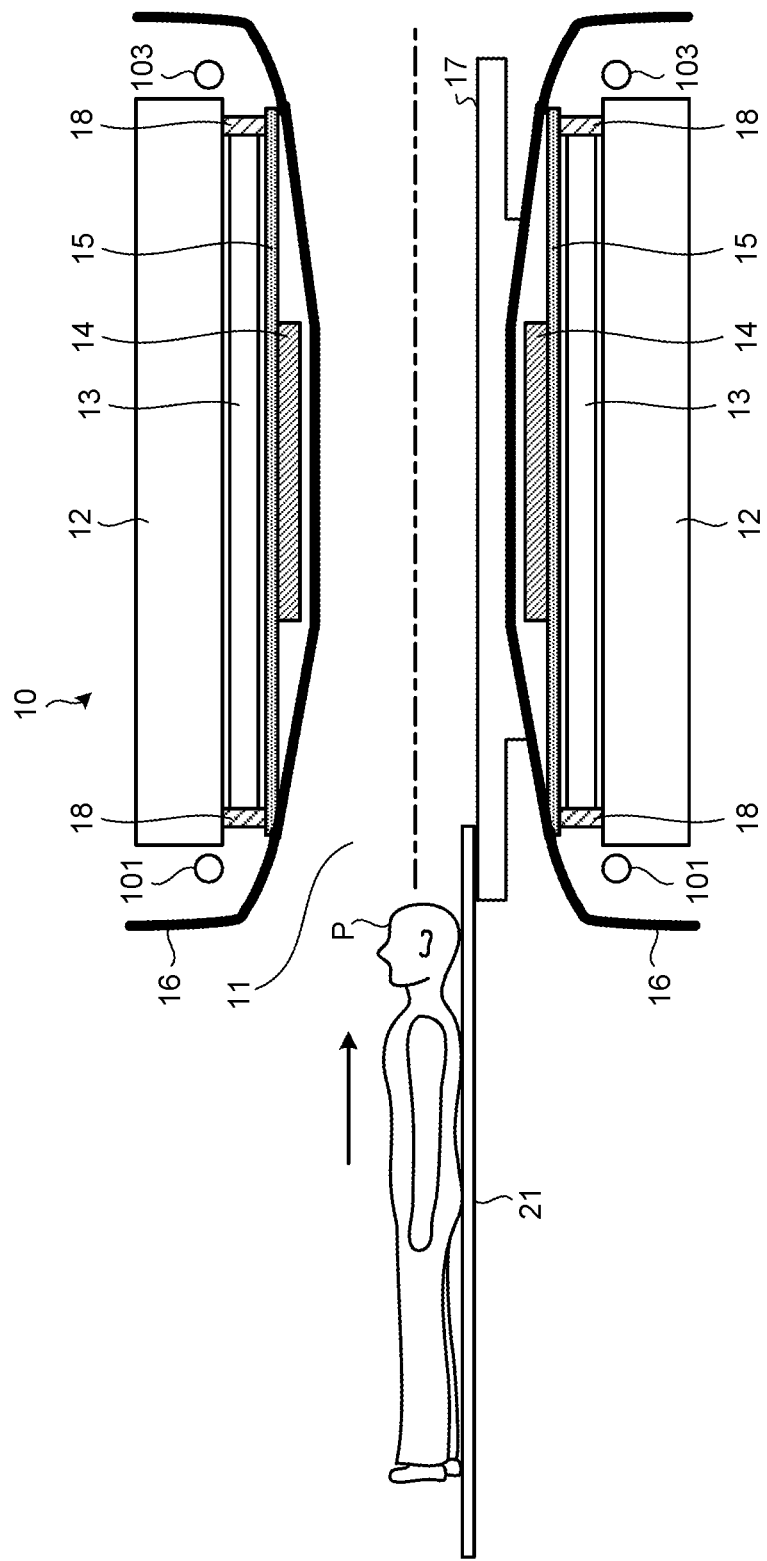
FIG. 2 is a drawing for explaining an exemplary configuration of a gantry device according to the embodiment.

According to the present embodiment, the gantry device 10 is configured in the manner described below, in order to ensure comfortableness of subjects during image-capturing processes. FIG. 2 is a drawing for explaining an exemplary configuration of the gantry device according to the present embodiment. FIG. 2 is a cross-sectional view obtained by sectioning the gantry device 10 shown in FIG. 1 along the insertion direction of the couchtop 21.

First, as shown in FIG. 2, the gantry device 10 according to the present embodiment includes a magnetostatic field magnet 12, a gradient coil 13, and a transmission RF coil 14.

The magnetostatic field magnet 12 is a magnet that generates a uniform magnetostatic field in the space inside the bore 11. For example, when superconducting magnet is used, the magnetostatic field magnet 12 is principally formed in the shape of a hollow circular cylinder. A permanent magnet may also be used instead.

The gradient coil 13 is disposed on the inside of the magnetostatic field magnet 12. When the magnetostatic field magnet 12 is in the commonly-used shape of a hollow circular cylinder, the gradient coil 13 is also formed in the shape of a hollow circular cylinder. The gradient coil 13 is formed by combining three coils corresponding to X-, Y-, and Z-axes that are orthogonal to one another. These three coils individually receive a supply of electric current from a power source of the gradient magnetic field and generate gradient magnetic fields of which the magnetic field intensities change along the X-, Y-, and Z-axes. It is assumed that the Z-axis direction is the same as the direction of the magnetostatic field.

For example, the gradient coil 13 is an ASGC. End faces of the gradient coil 13 are covered by sound-blocking lids 18, as shown in FIG. 2.

The transmission RF coil 14 is a coil disposed on the inside of the gradient coil 13 and generates a high-frequency magnetic field by using a high-frequency pulse supplied from a transmitting unit (not shown in the figures).

Here, as shown in FIG. 2, the magnetostatic field magnet 12, the gradient coil 13, and so forth are disposed on the outside of a bore tube 15 having a hollow circular cylindrical shape, to secure the space of the bore 11. In the example shown in FIG. 2, the transmission RF coil 14 is disposed on the inside of the bore tube 15.

A cover 16 is provided as an exterior casing of the gantry device 10. In the example shown in FIG. 2, the magnetostatic field magnet 12, the gradient coil 13, the transmission RF coil 14, and so forth are housed in the cover 16.

Furthermore, a rail 17 etc. on which the couchtop 21 is moved is provided in the bore 11 of the gantry device 10. Alternatively, the transmission RF coil 14 may be disposed inside the bore 11.

Furthermore, in the present embodiment, as shown in FIG. 2, front light sources 101 are provided in the surroundings of a front opening, which is an opening of the bore 11 and is positioned at the front of the couch device 20. The front opening is the opening on the left-hand side of FIG. 2.

Furthermore, in the present embodiment, as shown in FIG. 2, rear light sources 103 are provided in the surroundings of a rear opening, which is an opening of the bore 11 and is positioned on the side opposite from the front opening. The front opening is the opening on the left-hand side in the case of FIG. 2.

First, the front light sources 101 will be explained. By providing the front light sources 101, it is possible to make the portion of the cover 16 positioned near the front opening brighter than the surroundings thereof. Because the portion of the cover 16 positioned near the front opening is illuminated, the subject P feels that the front opening is large, while the subject P is moved into the bore 11.

Figure 4A:
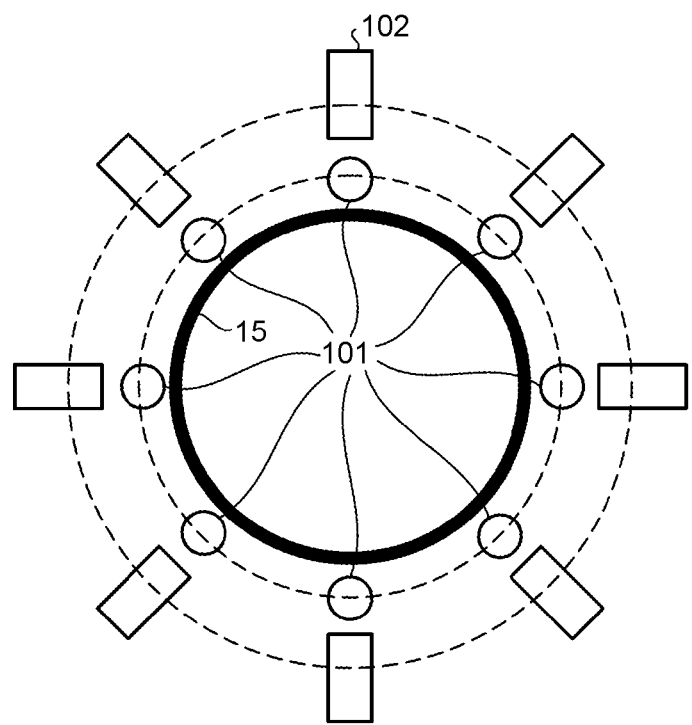
FIG. 4A is a second drawing for explaining the front light sources and the front reflecting units according to the embodiment.
Figure 4B:
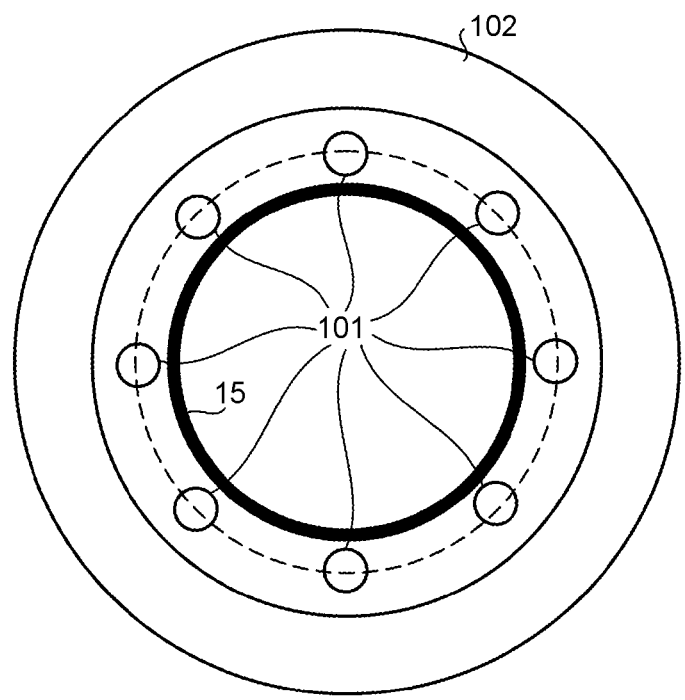
FIG. 4B is a third drawing for explaining the front light sources and the front reflecting units according to the embodiment.

Here, to brighten the front opening efficiently, front reflecting units 102 are further provided in the gantry device 10 according to the present embodiment, the front reflecting units 102 being configured to guide the light emitted from the front light sources 101 toward the couch device 20 side by reflecting the light with reflecting members. FIGS. 3, 4A, and 4B are drawings for explaining the front light sources and the front reflecting units according to the present embodiment. FIG. 3 is an enlarged view of surroundings of the front opening of the gantry device 10 shown in FIG. 2. FIGS. 4A and 4B are each a cross-sectional view obtained by sectioning surroundings of the front opening of the gantry device 10 shown in FIG. 2, at a cross-sectional plane orthogonal to the insertion direction of the couchtop 21.

As shown in FIG. 3, the front reflecting units 102 guide the light emitted from the front light sources 101 toward the couch device 20 side, by reflecting the light with the reflecting members. In other words, each of the front reflecting units 102 shown in FIG. 3 is a reflector, and the surface thereof or the entirety thereof is configured with a reflecting member. As shown in FIG. 3, the surface of each of the front reflecting units 102 is shaped in a serrated form, for example, so that the light emitted from the front light sources 101 advances toward the portion of the cover 16 positioned at the front face of the gantry device 10. The shape of the surface of each of the front reflecting units 102 is not limited to the serrated form. As long as the light emitted from the front light sources 101 is guided toward the couch device 20 side, the surface of the front reflecting units 102 may have an arbitrary shape.

Here, as shown in FIG. 3, the front reflecting units 102 are attached to the sound-blocking lid 18 that is attached to one end of the gradient coil 13. Alternatively, the front reflecting units 102 may be integrally formed so as to serve as the sound-blocking lid 18.

Furthermore, in the present embodiment, the multiple front light sources 101 are provided along the aperture of the bore 11 on the inside of the cover 16 of the gantry device 10. Furthermore, in the present embodiment, the front reflecting units 102 are provided along the aperture of the bore 11 on the inside of the cover 16 of the gantry device 10. For example, eight front light sources 101 are provided at regular intervals on a concentric circle centered on the center of the bore tube 15, as shown in FIGS. 4A and 4B.

Furthermore, as shown in FIG. 4A, eight front reflecting units 102 are attached at regular intervals to the sound-blocking lid 18 on the front opening side so as to correspond to the eight front light sources 101, respectively. The sound-blocking lid 18 is attached to the gradient coil 13 positioned on a concentric circle centered on the center of the bore tube 15. Thus, the eight front reflecting units 102 are also provided at regular intervals on a concentric circle centered on the center of the bore tube 15.

Alternatively, as shown in FIG. 4B, one front reflecting unit 102 may be shaped in a ring form that fits around the inside diameter of the bore tube 15 and be attached to the sound-blocking lid 18 on the front opening side, so as to comprehensively reflect the light emitted from each of the eight front light sources 101.

According to the present embodiment, the gantry device 10 is configured in the manner described below to efficiently brighten the portion of the cover 16 positioned near the front opening: Such a portion of the cover 16 of the gantry device 10 that is illuminated by the light emitted from the front light sources 101 is made of a transparent or translucent material. Here, the portion of the cover 16 that is illuminated by the light emitted from the front light sources 101 may include a portion of the cover 16 that is directly illuminated by the light emitted from the front light sources 101 and a portion of the cover 16 that is illuminated by the light emitted from the front light sources 101 and reflected by the front reflecting units 102. The portion made of the transparent or translucent material may be both of the two portions or may be one of the two portions.

Next, the rear light sources 103 will be explained. The rear light sources 103 being provided, it is possible to make the portion of the cover 16 positioned near the rear opening brighter than the surroundings thereof. Because the portion of the cover 16 in the rear part inside the bore 11 is illuminated, the subject P moving through the bore 11 moves from a darker place to a brighter place. Thus, due to what is called a savannah effect, the subject P is able to move through the bore 11 while feeling secure.

Figure 6A:
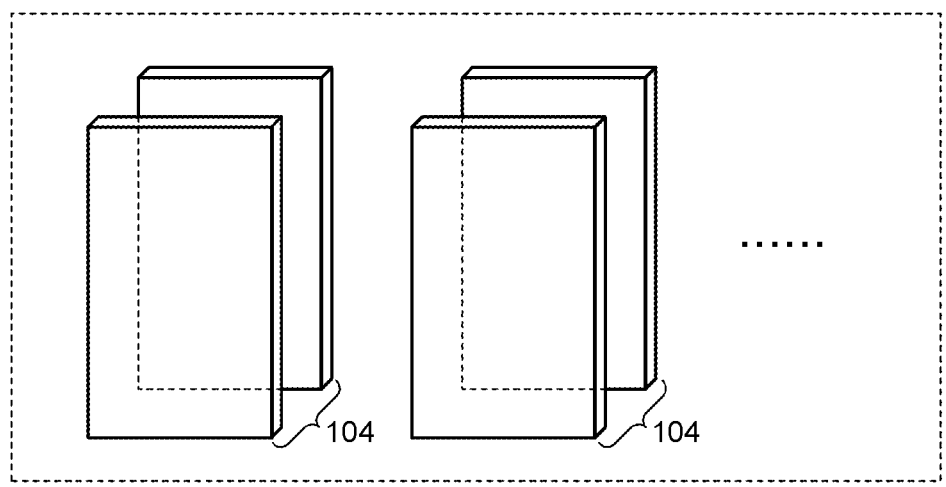
FIG. 6A is a second drawing for explaining the rear light sources and the rear reflecting units according to the embodiment.
Figure 6B:
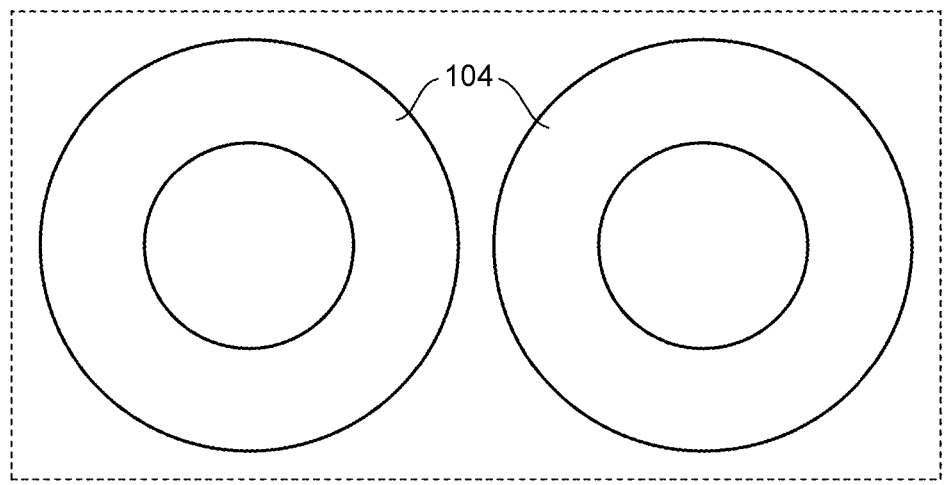
FIG. 6B is a third drawing for explaining the rear light sources and the rear reflecting units according to the embodiment.

To efficiently brighten the portion of the cover 16 in the rear part inside the bore 11, rear reflecting units 104 are further provided in the gantry device 10 according to the present embodiment, the rear reflecting units 104 being configured to guide the light emitted from the rear light sources 103 to the inside of the bore 11 by reflecting the light between two reflecting members facing each other. FIGS. 5, 6A, and 6B are drawings for explaining the rear light sources and the rear reflecting units according to the present embodiment. FIG. 5 is an enlarged view of surrounding of the rear opening of the gantry device 10 shown in FIG. 2. FIGS. 6A and 6B are each a cross-sectional view obtained by sectioning surroundings of the rear opening of the gantry device 10 shown in FIG. 2, at a cross-sectional plane orthogonal to the insertion direction of the couchtop 21.

As shown in FIG. 5, the rear reflecting units 104 guide the light emitted from the rear light sources 103 to the inside of the bore 11 by reflecting the light between the two reflecting members facing each other. In other words, each of the rear reflecting units 104 shown in FIG. 5 is a reflector, and the surface thereof or the entirety thereof is configured with a reflecting member. As shown in FIG. 5, the rear reflecting units 104 include the two reflecting members that have interposed therebetween an optical path of the light from the rear light sources 103, so that the light emitted from the rear light sources 103 advances toward the portion of the cover 16 positioned at the rear of the bore tube 15.

In this situation, as shown in FIG. 5, the rear reflecting units 104 are attached to the sound-blocking lid 18 that is attached to one end of the gradient coil 13. Alternatively, the rear reflecting units 104 may be integrally formed so as to serve as the sound-blocking lid 18.

Furthermore, in the present embodiment, the multiple rear light sources 103 are provided along the aperture of the bore 11 on the inside of the cover 16 of the gantry device 10. Furthermore, in the present embodiment, the rear reflecting units 104 are provided along the aperture of the bore 11 on the inside of the cover 16 of the gantry device 10. For example, eight rear light sources 103 are provided at regular intervals on a concentric circle centered on the center of the bore tube 15, similarly to the front light sources 101.

Furthermore, as shown in FIG. 6A, the multiple rear reflecting units 104 each having a pair of reflecting members are provided so as to correspond to the eight rear light sources 103. In other words, eight rear reflecting units 104 each having a pair of reflecting members are attached at regular intervals to the sound-blocking lid 18 on the rear opening side on a concentric circle centered on the center of the bore tube 15.

Alternatively, as shown in FIG. 6B, one pair of rear reflecting units 104 may be shaped in a ring form that fits around the inside diameter of the bore tube 15 and be attached to the sound-blocking lid 18 on the rear opening side, so as to comprehensively reflect the light emitted from each of the eight rear light sources 103.

According to the present embodiment, the gantry device 10 is configured in the manner described below to efficiently brighten the portion of the cover 16 positioned near the rear opening: Such a portion of the cover 16 of the gantry device 10 that is illuminated by the light emitted from the rear light sources 103 is made of a transparent or translucent material. The portion of the cover 16 that is illuminated by the light emitted from the rear light sources 103 may include a portion of the cover 16 that is directly illuminated by the light emitted from the rear light sources 103 and a portion of the cover 16 that is illuminated by the light emitted from the rear light sources 103 and reflected by the rear reflecting units 104. The portion made of the transparent or translucent material may be both of these portions or may be one of these portions.

As explained above, according to the present embodiment, by brightening the entrance of the bore 11 by using the front light sources 101, it is possible to create the feeling that the front opening is large. Furthermore, according to the present embodiment, by efficiently brightening the front of the entrance of the bore 11 by using the front reflecting units 102, it is possible to create the feeling that the front opening is even larger. Consequently, according to the present embodiment, it is possible to make the subject P feel secure when the subject P goes into the bore 11 during the image-capturing process.

Furthermore, according to the present embodiment, by brightening the exit of the bore 11 by using the rear light sources 103 so that the subject P is moved toward a bright place, it is possible to make the subject P feel secure with the savannah effect. Furthermore, according to the present embodiment, by efficiently brightening the inside of the bore 11 near the exit by using the rear reflecting units 104, it is possible to make the subject P feel even more secure with an additional savannah effect. Consequently, according to the present embodiment, it is possible to make the subject P feel secure when the subject P is moved through the bore 11 during the image-capturing process. As a result, according to the present embodiment, it is possible to ensure comfortableness of the subject P during the image-capturing process.

Furthermore, according to the present embodiment, because the front light sources 101 and the front reflecting units 102 as well as the rear light sources 103 and the rear reflecting units 104 are positioned along the aperture of the bore, the subject P, who is placed on the couchtop 21, is able to perceive the light, regardless of his/her posture. Consequently, according to the present embodiment, it is possible to ensure comfortableness of the subject P in correspondence with image-capturing processes performed on various postures of the subject.

Furthermore, according to the present embodiment, by attaching the front reflecting units 102 and the rear reflecting units 104 to the sound-blocking lids 18 or by forming the front reflecting units 102 and the rear reflecting units 104 integrally with the sound-blocking lids 18, it is possible to effectively utilize the space inside the cover 16.

It should be noted that it is desirable to configure the front reflecting units 102 and the rear reflecting units 104 by using a non-magnetic material, so that no vibration etc. is caused by the magnetic fields generated inside the gantry device 10.

Furthermore, according to the present embodiment, the portion of the cover 16 of the gantry device 10 that is illuminated by the light emitted from the front light sources 101 is made of the transparent or translucent material. Furthermore, according to the present embodiment, the portion of the cover 16 of the gantry device 10 that is illuminated by the light emitted from the rear light sources 103 is made of the transparent or translucent material. Consequently, according to the present embodiment, it is possible to efficiently brighten the portion of the cover 16 positioned near the front opening and the inside of the portion of the cover 16 positioned near the rear opening.

Alternatively, to efficiently brighten the portion of the cover 16 positioned near the front opening and the inside of the portion of the cover 16 positioned near the rear opening, it is also possible to configure the present embodiment so that such a portion of the cover 16 of the gantry device 10 that forms the bore 11 (i.e., the bore tube 15) is made of a transparent or translucent material. Furthermore, it is also possible to configure the rail 17 which is provided inside the bore 11 and on which the couchtop 21 is moved, by using a transparent or translucent material.

Figure 7:
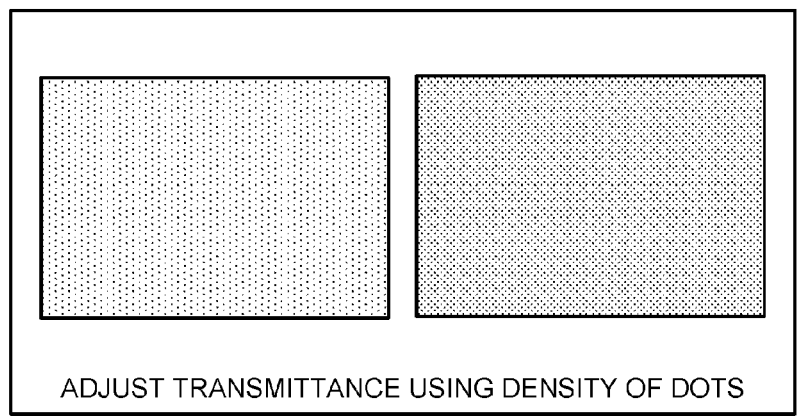
FIG. 7 is a drawing for explaining an example of a method for arranging a cover to be translucent according to the embodiment.

Furthermore, the cover 16 may be arranged to be translucent by performing the following process: A transparent material is shaped to form the cover 16, and subsequently the transmittance thereof is changed by applying a back-coating process or a printing process thereto so as to arrange a part or the entirety of the cover 16 to be translucent. The portion arranged to be translucent includes, as mentioned above, the portion that is illuminated by the light emitted from the front light sources 101 and the portion that is illuminated by the light emitted from the rear light sources 103. FIG. 7 is a drawing for explaining an example of a method for arranging the cover to be translucent according to the present embodiment. For example, it is possible to shape a transparent material to form the cover 16 and to subsequently change the density of printed dots, so as to arrange a part or the entirety of the cover 16 to be translucent. In that situation, as shown in FIG. 7, the cover 16 is arranged to be translucent through an adjustment of the transmittance, the adjustment of the transmittance being performed by changing the density of the printed dots. Furthermore, it is also possible to arrange the bore tube 15 to be translucent, by shaping a transparent material and subsequently changing the transmittance thereof by applying a back-coating process or a printing process thereto.

Figure 8:
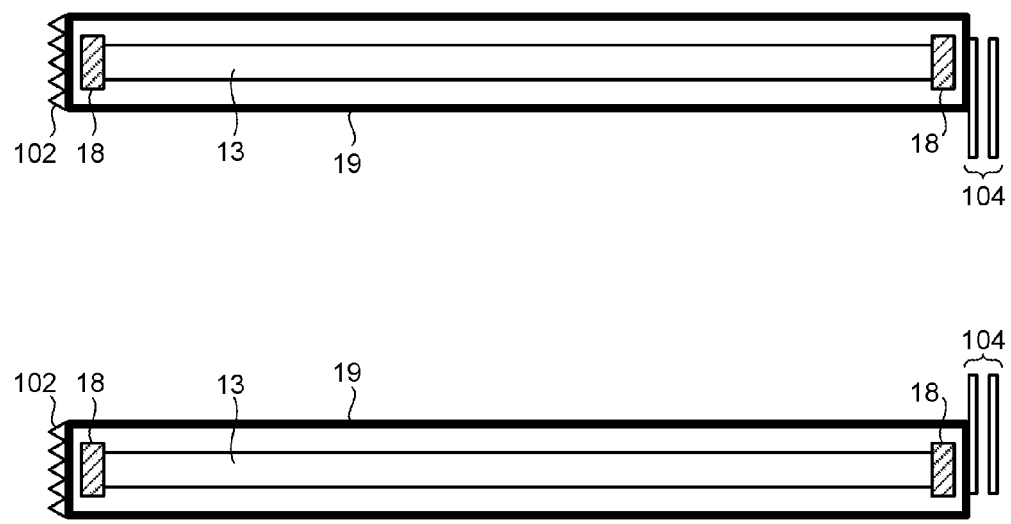
FIG. 8 is a drawing for explaining a modification example of locations where the front reflecting units and the rear reflecting units are provided.

Furthermore, in the embodiment described above, the example is explained in which the front reflecting units 102 and the rear reflecting units 104 are attached to the sound-blocking lids 18; however, it is possible to configure the present embodiment in such a manner that the front reflecting units 102 and the rear reflecting units 104 are separately provided in positions distant from the sound-blocking lids 18. Furthermore, it is also possible to configure the present embodiment in such a manner that the front reflecting units 102 and the rear reflecting units 104 are attached to another constituent element of the gantry device 10 or are integrally formed so as to serve as another constituent element of the gantry device 10. FIG. 8 is a drawing for explaining a modification example of the locations where the front reflecting units and the rear reflecting units are provided.

For example, the gradient coil 13 shown in FIG. 8 is configured so that the sound-blocking lids 18 are attached to the end faces, and the assembly is further stored in a vacuum container 19. In that situation, as shown in FIG. 8, the front reflecting units 102 are attached to the vacuum container 19. Furthermore, as shown in FIG. 8, the rear reflecting units 104 are also attached to the vacuum container 19. Alternatively, the front reflecting units 102 and the rear reflecting units 104 may be integrally formed so as to serve as the vacuum container 19. With these arrangements also, it is possible to effectively utilize the space inside the cover 16.

The electric power supply to the front light sources 101 and the rear light sources 103 may be started by the operator of the MRI apparatus 1 or may be automatically started at the point in time when the couchtop 21 starts moving. The automatic control in this situation is exercised by, for example, the controlling device 30 that controls operations of the couchtop 21 and so forth.

Figure 9:
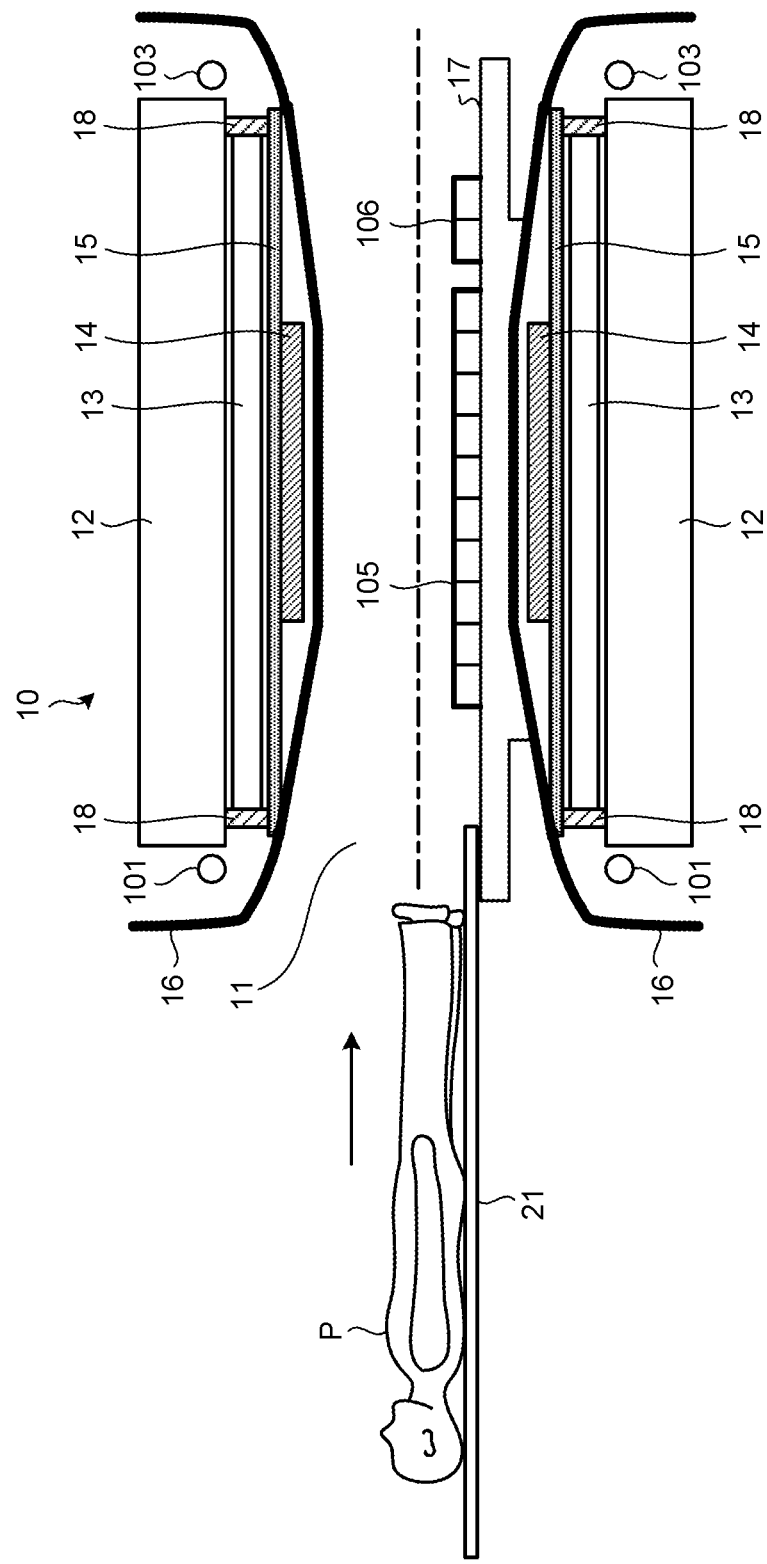
FIG. 9 is a drawing of an example of multiple illuminating elements provided on the inside of a bore, according to another modification example of the embodiment.

In the embodiment described above, as for the illumination for the openings, the example is explained in which the front light sources 101 and the rear light sources 103 are provided in the two locations, i.e., in the surroundings of the front opening and the surroundings of the rear opening. However, it is also possible to configure the embodiment described above in such a manner that at least one more illuminating element is provided inside the bore 11, in addition to the front light sources 101 and the rear light sources 103. In other words, it is possible to configure the present embodiment in such a manner that one or more illuminating elements for the inside of the bore 11 are provided, together with the illumination for the openings. FIG. 9 is a drawing of an example of a plurality of illuminating elements provided on the inside of the bore, according to another modification example of the present embodiment.

For example, according to the present modification example, as shown in FIG. 9, a first illuminating element 105 and a second illuminating element 106 are provided as the illuminating elements for the inside of the bore 11. As shown in FIG. 9, the first illuminating element 105 and the second illuminating element 106 are positioned along the longitudinal direction of the bore 11 so as to extend along the rail 17 on which the couchtop 21 is moved. As shown in FIG. 9, the first illuminating element 105 is provided on the front opening side inside the bore 11, whereas the second illuminating element 106 is provided on the rear opening side inside the bore 11. Although not shown in the drawings, the first illuminating element 105 is provided in two locations on both sides of the rail 17 in such a position that does not hinder the movement of the couchtop 21. The second illuminating element 106 is provided in two locations on both sides of the rail 17 in such a position where the couchtop 21 is able to move.

The first illuminating element 105 and the second illuminating element 106 are configured to illuminate the inside of the bore 11 and the upper surface and the lateral surfaces of the cover 16 inside the bore 11, by emitting light from the lower surface toward the upper surface of the bore 11. The first illuminating element 105 primarily illuminates an area centered on the center of the magnetic field on the inside of the bore 11. An image-capturing site of the subject P is usually positioned at the center of the magnetic field. The second illuminating element 106 primarily illuminates an area positioned between the illumination area of the first illuminating element 105 and the illumination area of the rear light sources 103, on the inside of the bore 11.

For example, the first illuminating element 105 and the second illuminating element 106 are each configured with a plurality of Light Emitting Diode (LED) lamps. Furthermore, the multiple LED lamps constituting the first illuminating element 105 are covered by a translucent cover. Similarly, the multiple LED lamps constituting the second illuminating element 106 are covered by a translucent cover. Because the translucent covers are used, the intense light emitted from the LED lamps become mild through the translucent covers. In other words, because the translucent covers are used, the inside of the bore 11 and the upper and lateral surfaces of the cover 16 inside the bore 11 are illuminated by the first illuminating element 105 and the second illuminating element 106, with the soft light that makes the subject P comfortable. The first illuminating element 105 and the second illuminating element 106 may each be configured by using an LED panel.

It is also possible to configure the present modification example in such a manner that the first illuminating element 105 and the second illuminating element 106 are structured by disposing light guiding members linearly along the rail 17, the light guiding members being configured to guide light emitted from a light source provided separately. The light guiding members may be configured by using optical fibers, for example. When the light guiding members are used, the upper and lateral surfaces of the cover 16 inside the bore 11 are illuminated by the first illuminating element 105 and the second illuminating element 106, with soft light that makes the subject P comfortable. Because the light guiding members do not get influenced by the magnetic fields, the light guiding members are useful as the illuminating elements provided on the inside of the bore 11.

It is possible to adjust the amount of light emitted from the LEDs. It is also possible to indirectly adjust the amount of light emitted from the light guiding members, by adjusting the amount of light generated the light source that supplies the light to the light guiding members. Furthermore, it is also possible to adjust the amount of light emitted from the front light sources 101 and from the rear light sources 103, by configuring the front light sources 101 and the rear light sources 103 by using LED lamps, for example.

In this situation, FIG. 2 illustrates an example in which an image-capturing process is performed by moving the subject P head first toward the inside of the bore 11. For example, an image-capturing process on the head/neck is performed head first. In contrast, FIG. 9 illustrates an example in which an image-capturing process is performed by moving the subject P feet first toward the inside of the bore 11. For example, an image-capturing process on the abdomen or the legs is performed feet first. Although it is also possible to perform an image-capturing process on the abdomen or the legs head first, the head of the subject P is inserted into the bore 11. To avoid making the subject P uncomfortable, it is preferable to arrange the head of the subject P to be outside the bore 11 whenever possible. Accordingly, the operator usually selects whether an image-capturing process is performed head first or feet first, depending on the image-capturing site. The decision made as to whether an image-capturing process is performed head first or feet first is input by the operator to the controlling device 30 as an image-capturing condition.

Figure 10:
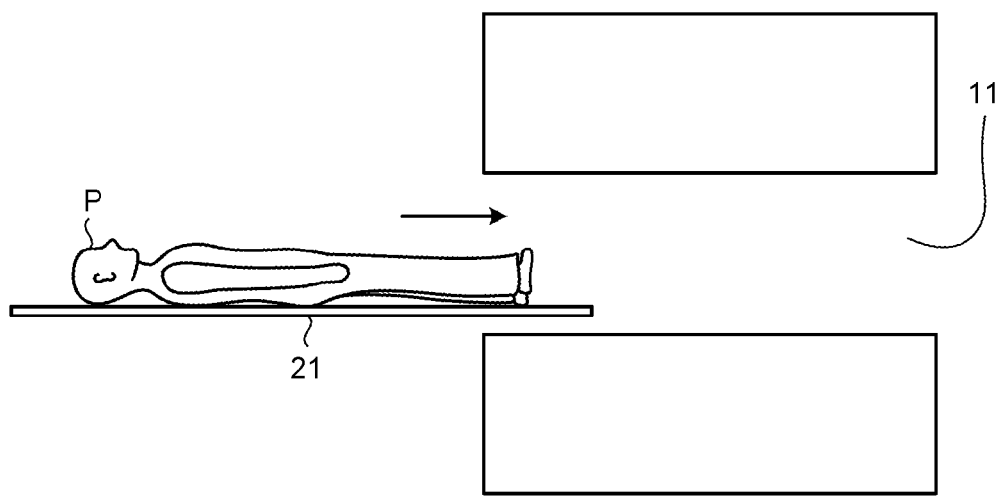
FIG. 10 is a first drawing of an example of light adjustment control exercised in the modification example of the embodiment.
Figure 11:
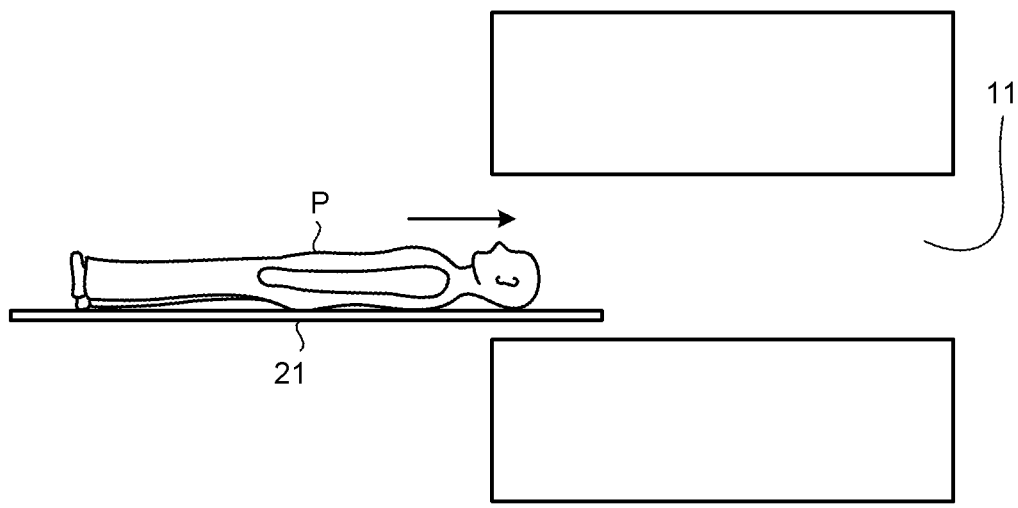
FIG. 11 is a second drawing of the example of the light adjustment control exercised in the modification example of the embodiment.

The area that can be viewed by the subject P who is placed on the couchtop 21 will be different depending on whether the image-capturing process is performed head first or feet first. Thus, in the present modification example in which the illuminating elements are provided inside the bore 11, control is further exercised in the following manner in order to ensure comfortableness of the subject during the image-capturing process: The controlling device 30 according to the present modification example performs a light adjusting process on the light emitted from the front light sources 101, the rear light sources 103, the first illuminating element 105, and the second illuminating element 106, depending on whether the subject P is moved head first or feet first. FIGS. 10 and 11 are drawings of examples of the light adjustment control exercised in the modification example of the embodiment.

For example, the light adjustment control exercised in the modification example of the embodiment is performed in correspondence with image-capturing steps, as well as with the image-capturing condition indicating whether the subject P is moved head first or feet first. For example, the image-capturing steps can roughly be grouped into the following four steps: The first step is a step from when the subject P enters an examination room where the gantry device 10 is installed, to when the subject P is placed on the couchtop 21. At the first step, the couchtop supporting unit 22 of the couch device 20 is moved to a lower position so that the subject P is able to move onto the couchtop 21 easily. The second step is a step from the end of the first step to when the couchtop 21 finishes being raised. At the second step, the couchtop supporting unit 22 is moved upward to a height equal to substantially the center of the bore 11. The third step is a step during which the couchtop 21 is inserted up to an image-capturing position. The fourth step is a step from the start to the end of the image-capturing process performed at an image-capturing site of the subject P. The controlling device 30 that controls operations of the couch device 20 is able to obtain information indicating what step is currently being performed.

First of all, at the first step, the controlling device 30 turns on all of the front light sources 101, the rear light sources 103, the first illuminating element 105, and the second illuminating element 106, both when the head first method is used and when the feet first method is used. At the first step, because the subject P is able to view the entirety of the gantry device 10, the controlling device 30 exercises light adjustment control to brighten the openings of the bore 11 and the entirety of the inside of the bore 11, regardless of whether the head first method is used or the feet first method is used.

Next, at the second step, the controlling device 30 keeps all of the front light sources 101, the rear light sources 103, the first illuminating element 105, and the second illuminating element 106 on, both when the head first method is used and when the feet first method is used, like at the first step. When the feet first method is used, the subject P is able to view the front opening and the inside of the bore. In contrast, when the head first method is used, the subject P views the ceiling of the examination room, but may also be able to view the front opening and the inside of the bore 11 depending on how his/her neck is bent. Thus, the controlling device 30 exercises light adjustment control to brighten the openings of the bore 11 and the entirety of the inside of the bore 11, also at the second step. However, when the head first method is used, it is difficult for the subject P to view the rear part inside the bore 11. Consequently, it is possible for the controlling device 30 to turn off the rear light sources 103, for example.

Next, at the third step during which the subject P is being moved through the bore 11, the controlling device 30 exercises light adjustment control differently for when the head first method is used and when the feet first method is used. FIG. 10 illustrates an example of the light adjustment control exercised by the controlling device 30 at the third step, when the feet first method is used. FIG. 11 illustrates an example of the light adjustment control exercised by the controlling device 30 at the third step, when the head first method is used. In FIGS. 10 and 11, "101" denotes the front light sources 101; "105" denotes the first illuminating element 105; "106" denotes the second illuminating element 106; and "103" denotes the rear light sources 103.

Furthermore, in FIGS. 10 and 11, "ON" indicates that the light sources or the illuminating element is on, whereas "OFF" indicates that the light sources or the illuminating element is off. In FIGS. 10 and 11, "ON (L)" indicates that the corresponding light sources or illuminating element is turned on with a small amount of light as a result of the light adjustment control, whereas "ON (H)" indicates that the corresponding light sources or illuminating element is turned on with a large amount of light as a result of the light adjustment control. Furthermore, in FIGS. 10 and 11, "ON (M)" indicates that the corresponding light sources or illuminating element is turned on with an amount of light being between that of "ON (L)" and that of "ON (H)", i.e., a medium amount of light, as a result of the light adjustment control.

At the third step during which the subject P is moved through the bore 11 feet first, as shown in FIG. 10, the front light sources 101 are turned on with a small amount of light, whereas the first illuminating element 105 is turned on with a medium amount of light, and the second illuminating element 106 and the rear light sources 103 are turned on with a large amount of light. When the feet first method is used, the subject P who is inserted into the bore 11 feet first is able to view the inside of the bore 11 from the front opening. Thus, the controlling device 30 exercises light adjustment control so that the amount of light increases from the front opening toward the rear opening, so as to achieve the savannah effect.

In contrast, at the third step during which the subject P is moved through the bore 11 head first, as shown in FIG. 11, the front light sources 101 and the rear light sources 103 are turned off, whereas the first illuminating element 105 and the second illuminating element 106 are turned on with a medium amount of light. When the head first method is used, the subject P who is inserted into the bore 11 head first primarily views the upper surface of the cover 16 inside the bore 11, while being moved. Thus, the illumination in the surroundings of the openings is not necessary, whereas the inside of the bore 11 should be illuminated with such an amount of light that makes the subject P comfortable. Alternatively, even when the head first method is used, in consideration of the possibility that the subject P may view the rear part of the bore 11, the controlling device 30 may, for example, turn on the first illuminating element 105 with a small amount of light and also turn on the second illuminating element 106 with a medium amount of light, so as to achieve the savannah effect.

Lastly, at the fourth step when the subject P is at a halt, the controlling device 30 turns off the front light sources 101 and turns on all of the rear light sources 103, the first illuminating element 105, and the second illuminating element 106, both when the head first method is used and when the feet first method is used. When the feet first method is used, because the subject P is able to view the inside of the bore 11 from the front opening, the controlling device 30 turns off the front light sources 101 and turns on all of the first illuminating element 105, the second illuminating element 106, and the rear light sources 103, so as to achieve the savannah effect even during the image-capturing process. In contrast, when the head first method is used, because the head of the subject P is positioned inside the bore 11, the controlling device 30 turns off the front light sources 101, which illuminates the outside of the field of vision of the subject P. The controlling device 30 turns on all of the first illuminating element 105, the second illuminating element 106, and the rear light sources 103 so as to brighten the entirety of the inside of the bore 11. Note that, when the head first method is used, because the subject P primarily views the upper surface of the cover 16 inside the bore 11, the controlling device 30 may turn off the rear light sources 103, for example.

As explained above, according to the present modification example, the plurality of illuminating elements are provided inside the bore 11, together with the front light sources 101 and the rear light sources 103. Furthermore, according to the present modification example, the light adjustment control is exercised on the plurality of illuminating elements so as to ensure comfortableness of the subject P, depending on whether the head first method is used or the feet first method is used. It is also possible to apply the modification example described above to the situation where the quantity of illuminating elements provided inside the bore 11 is one and the situations where the quantity is three or more. Alternatively, the light adjustment control explained in the modification example above may be exercised by another controlling device that is separately provided for light adjustment control purposes.

The features explained in the exemplary embodiments and the modification examples described above are also applicable to other medical image diagnosis apparatuses besides the MRI apparatus 1. The medical image diagnosis apparatuses to which the features described above are applicable each include a gantry device. The gantry device has a bore serving as a space where a medical image is captured and is configured to acquire data used for generating the medical image from a subject P when the subject P placed on a couchtop has been moved into the bore by a couch device configured to move the couchtop.

The medical image diagnosis apparatus may be, for example, an X-ray Computed Tomography (CT) apparatus, a Single Photon Emission Computed Tomography (SPECT) apparatus, or a Positron Emission computed Tomography (PET) apparatus. Alternatively, the medical image diagnosis apparatus may be, for example, a SPECT-CT apparatus in which a SPECT apparatus and an X-ray CT apparatus are integrated together, a PET-CT apparatus in which a PET apparatus and an X-ray CT apparatus are integrated together, or a PET-MRI apparatus in which a PET apparatus and an MRI apparatus are integrated together.

The constituent elements of the apparatuses and the devices that are shown in the drawings are based on functional concepts. Thus, it is not necessary to physically configure the elements as indicated in the drawings. In other words, the specific mode of distribution and integration of the apparatuses and the devices is not limited to the ones shown in the drawings. It is possible to functionally or physically distribute or integrate all or a part of the apparatuses and the devices in any arbitrary units, depending on various loads and the status of use.

As explained above, according to an aspect of the present embodiments, it is possible to ensure comfortableness of the subject during the image-capturing process.

While certain embodiments have been described, these embodiments have been presented by way of example only, and are not intended to limit the scope of the inventions. Indeed, the novel embodiments described herein may be embodied in a variety of other forms; Furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
    a gantry device having a bore serving as a space where a magnetic resonance image is captured, with the gantry device being configured to acquire, when a subject placed on a couchtop has been moved into the bore by a couch device configured to move the couchtop, a magnetic resonance signal from the subject;
    a front light source provided in surroundings of a front opening, with the front opening being an opening of the bore, and with the front opening being an opening of the bore positioned at front of the couch device; and
    an exterior casing of the gantry device, with a portion of the exterior casing being illuminated by light emitted from the front light source, and with the portion of the exterior casing being made of a transparent or translucent material;
    a front reflecting unit configured to guide the light emitted from the front light source to a couch device side by reflecting the light with a reflecting member; and
    a sound-blocking lid attached to an end of a gradient coil included in the gantry device,
    wherein the front reflecting unit is either attached to the sound-blocking lid or integrally formed so as to serve the sound-blocking lid.

2. The magnetic resonance imaging apparatus according to claim 1, wherein multiple front light sources are provided along an aperture of the bore on an inside of the exterior casing of the gantry device.

3. The magnetic resonance imaging apparatus according to claim 2, further comprising:
    a front reflecting unit configured to guide the light emitted from the front light sources to a couch device side by reflecting the light with a reflecting member, wherein
    the front reflecting unit is provided along the aperture of the bore on the inside of the exterior casing of the gantry device.

4. The magnetic resonance imaging apparatus according to claim 1, wherein the front reflecting unit is made of a nonmagnetic material.

5. The magnetic resonance imaging apparatus according to claim 1, wherein a portion of the exterior casing of the gantry device that forms the bore is made of a transparent or translucent material.

6. The magnetic resonance imaging apparatus according to claim 1, wherein a part or an entirety of the exterior casing of the gantry device is arranged to be translucent by shaping a transparent material and further by changing a transmittance thereof by applying a back-coating process or a printing process thereto.

7. The magnetic resonance imaging apparatus according to claim 6, wherein the part or the entirety of the exterior casing of the gantry device is arranged to be translucent by changing a density of printed dots.

8. A magnetic resonance imaging apparatus comprising:
a gantry device having a bore serving as a space where a magnetic resonance image is captured, with the gantry device being configured to acquire, when a subject placed on a couchtop has been moved into the bore by a couch device configured to move the couchtop, a magnetic resonance signal from the subject;
a front light source provided in surroundings of a front opening, with the front opening being an opening of the bore, and with the front opening being an opening of the bore positioned at front of the couch device;
an exterior casing of the gantry device, with a portion of the exterior casing being illuminated by light emitted from the front light source, and with the portion of the exterior casing being made of a transparent or translucent material;
a front reflecting unit configured to guide the light emitted from the front light source to a couch device side by reflecting the light with a reflecting member; and
a vacuum container storing therein a gradient coil included in the gantry device, wherein
the front reflecting unit is either attached to the vacuum container or integrally formed so as to serve as the vacuum container.

9. A magnetic resonance imaging apparatus comprising:
a gantry device having a bore serving as a space where a magnetic resonance image is captured, with the gantry device being configured to acquire, when a subject placed on a couchtop has been moved into the bore by a couch device configured to move the couchtop, a magnetic resonance signal from the subject;
a front light source provided in surroundings of a front opening, with the front opening being an opening of the bore, and with the front opening being an opening of the bore positioned at front of the couch device;
an exterior casing of the gantry device, with a portion of the exterior casing being illuminated by light emitted from the front light source, and with the portion of the exterior casing being made of a transparent or translucent material; and
a rear light source provided in surroundings of a rear opening being an opening of the bore, with the rear opening being an opening of the bore positioned on a side opposite from the front opening, wherein
a portion of the exterior casing of the gantry device that is illuminated by light emitted from the rear light source is further made of a transparent or translucent material.

10. The magnetic resonance imaging apparatus according to claim 9, further comprising:
a rear reflecting unit configured to guide the light emitted from the rear light source to an inside of the bore, by reflecting the light between two reflecting members facing each other.

11. The magnetic resonance imaging apparatus according to claim 10, further comprising:
a sound-blocking lid attached to an end of a gradient coil included in the gantry device, wherein
the rear reflecting unit is either attached to the sound-blocking lid or integrally formed so as to serve as the sound-blocking lid.

12. The magnetic resonance imaging apparatus according to claim 10, further comprising:
a vacuum container storing therein a gradient coil included in the gantry device, wherein
the rear reflecting unit is either attached to the vacuum container or integrally formed so as to serve as the vacuum container.

13. The magnetic resonance imaging apparatus according to claim 9, wherein multiple rear light sources are provided along an aperture of the bore on an inside of the exterior casing of the gantry device.

14. The magnetic resonance imaging apparatus according to claim 13, further comprising:
a rear reflecting unit configured to guide the light emitted from the rear light sources to an inside of the bore by reflecting the light between two reflecting members facing each other, wherein
the rear reflecting unit is provided along the aperture of the bore on the inside of the exterior casing of the gantry device.

15. The magnetic resonance imaging apparatus according to claim 10, wherein the rear reflecting unit is made of a nonmagnetic material.

16. The magnetic resonance imaging apparatus according to claim 9, further comprising:
at least one illuminating element being provided inside the bore; and
a controlling device configured to perform a light adjusting process on light emitted from the front light source, the rear light source, and said at least one illuminating element, in accordance with whether the subject is moved toward an inside of the bore head first or feet first.

17. A magnetic resonance imaging apparatus comprising:
a gantry device having a bore serving as a space where a magnetic resonance image is captured, with the gantry device being configured to acquire, when a subject placed on a couchtop has been moved into the bore by a couch device configured to move the couchtop, a magnetic resonance signal from the subject;
a front light source provided in surroundings of a front opening, with the front opening being an opening of the bore, and with the front opening being an opening of the bore positioned at front of the couch device; and
an exterior casing of the gantry device, with a portion of the exterior casing being illuminated by light emitted from the front light source, and with the portion of the exterior casing being made of a transparent or translucent material,
wherein a rail which is provided in the bore and on which the couchtop is moved is made of a transparent or translucent material.

18. A medical image diagnosis apparatus comprising:
a gantry device having a bore serving as a space where a medical image is captured, with the gantry device being configured to acquire, when a subject placed on a couchtop has been moved into the bore by a couch device configured to move the couchtop, data used for generating the medical image from the subject;
a front light source provided in surroundings of a front opening being an opening of the bore, with the front opening being an opening of the bore positioned at front of the couch device; and
an exterior casing of the gantry device, with a portion of the exterior casing being illuminated by light emitted from the front light source, with the portion of the exterior casing being made of a transparent or translucent material,
a front reflecting unit configured to guide the light emitted from the front light source to a couch device side by reflecting the light with a reflecting member; and
a sound-blocking lid attached to an end of a gradient coil included in the gantry device, wherein
the front reflecting unit is either attached to the sound-blocking lid or integrally formed so as to serve as the sound-blocking lid.

* * * * *